United States Patent [19]

Lin et al.

[11] Patent Number: 4,808,748

[45] Date of Patent: Feb. 28, 1989

[54] TRIFLUOROMETHYLATION PROCESS

[75] Inventors: Ronny W. Lin; Robert I. Davidson, both of Baton Rouge, La.

[73] Assignee: Ethyl Corporation, Richmond, Va.

[21] Appl. No.: 808,304

[22] Filed: Dec. 12, 1985

[51] Int. Cl.$^4$ ............................................ C07F 120/00
[52] U.S. Cl. .................................... 558/378; 560/100; 570/144
[58] Field of Search ................ 558/423, 378; 560/100; 570/144

[56] References Cited

U.S. PATENT DOCUMENTS 4,439,617  3/1984  Sesianj et al. ........................ 560/39
4,590,010  5/1986  Ramachandran et al. ......... 558/341

OTHER PUBLICATIONS

Matsui et al., "Chemistry Letters", (1981) pp. 1719–1720.

Primary Examiner—Anton H. Sutto
Attorney, Agent, or Firm—Patricia J. Hogan

[57] ABSTRACT

Trifluoromethylaromatic compounds are prepared by reacting the corresponding aromatic bromide or iodide with potassium trifluoroacetate in the presence of cuprous iodide and a dipolar aprotic solvent.

20 Claims, No Drawings

TRIFLUOROMETHYLATION PROCESS

FIELD OF INVENTION

This invention relates to trifluoromethylaromatic compounds and more particularly to a process for preparing them.

BACKGROUND

As disclosed in Matsui et al., *Chemistry Letters*, 1981, pp. 1719-1720, it is known that aromatic iodides can be trifluoromethylated by reacting them with a large excess of sodium trifluoroacetate in the presence of cuprous iodide and a dipolar aprotic solvent. Matsui et al. also show that some trifluoromethylation occurs when an aromatic bromide is employed in the reaction instead of an iodide but that the yield of product is quite low.

Copending application Ser. No. 724,474 (Ramachandran et al.), filed Apr. 18, 1985, now U.S. Pat. No. 4,590,010, teaches that the technique of Matsui et al. is applicable to the trifluoromethylation of 6-alkoxy-5-halo-1-cyanonaphthalenes and the corresponding naphthoate esters—compounds which, like the compounds of Matsui et al., give better yields of the desired products when the halo substituent is iodo. Ramachandran et al. indicate that other trifluoroacetate salts can be used in their process, but they disclose a preference for using sodium trifluoroacetate as the trifluoromethylating agent.

It has been found that the use of sodium trifluoroacetate as a trifluoromethylating agent has several disadvantages. As mentioned above, sodium trifluoroacetate has to be used in considerable excess, and it does not provide acceptable yields of product from aromatic bromides. Moreover, its use requires a longer reaction time than would be desired, and it leads to the formation of relatively large amounts of by-products.

SUMMARY OF INVENTION

An object of this invention is to provide a novel process for preparing trifluoromethylaromatic compounds.

Another object is to provide such a process wherein the trifluoromethylaromatic compounds can be prepared in high yields from aromatic iodides or aromatic bromides.

A further object is to provide such a process which utilizes a trifluoromethylating agent that is more selective than sodium trifluoroacetate, can be used in smaller amounts, and does not require as long a reaction time.

These and other objects are attained by reacting an aromatic bromide or iodide with potassium trifluoroacetate in the presence of cuprous iodide and a dipolar aprotic solvent.

DETAILED DESCRIPTION

Aromatic halides utilizable in the practice of the invention are substituted and unsubstituted aromatic iodides and bromides wherein any substituents are inert substituents (i.e., substituents that do not prevent the reaction from occurring) such as alkyl, alkoxy, alkylthio, aryl, aryloxy, arylthio, cyano, nitro, acylamino, akylamino, tertiary amino, sulfonamido, sulfone, sulfonyl, phosphino, perfluoroalkyl, chloro, fluoro, ester, aldehyde, ketone, acetal, sulfono groups, etc., and the aromatic ring may be a carboxylic ring such as a benzene, naphthalene, anthracene, etc., ring or a five- or six-membered heterocyclic ring having aromatic character, e.g., a pyridine, quinoline, isoquinoline, thiophene, pyrrole, furan, etc., ring. Exemplary of such compounds are iodobenzene, 3-iodotoluene, 4-chloroiodobenzene, 4-iodomethoxybenzene, 1-iodonaphthalene, 3-iodoaniline, 1-iodo-3-nitrobenzene, 2-iodothiophene, 4-iodoisoquinoline, 2-iodopyridine, 3-iodoquinoline, the corresponding bromides, etc.

In a preferred embodiment of the invention, the aromatic halide is a halonaphthalene corresponding to the formula:

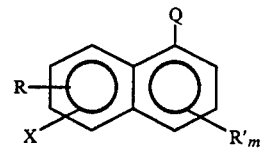

wherein R and R' are independently selected from chloro, fluoro, nitro, hydroxy, and alkyl and alkoxy substituents containing 1-6 carbons; Q is —CN or —COOR''; R'' is saturated hydrocarbyl; X is bromo or iodo; and m is 0 or 1.

The halocyanonaphthalenes and halonaphthoates utilizable in the practice of the invention may be any compounds corresponding to the above halonaphthalene formula, but they are preferably compounds wherein m is 0, X is in the 5-position, and R is an alkyl or alkoxy substituent in the 6-position. When the R and R' substituents are alkyl or alkoxy, they are generally straight-chain groups of 1-3 carbons or branched-chain groups of three or four carbons, such as methyl, ethyl, propyl, 1-methylethyl, butyl, 2-methylpropyl, 1,1-dimethylethyl, the corresponding alkoxy groups, etc., although, as indicated above, larger groups such as hexyl and hexanoxy are also utilizable. When the halonaphthalene is an ester, R'' may be any saturated hydrocarbyl group (i.e., a hydrocarbyl group that is free of aliphatic unsaturation) but is preferably an alkyl, cycloalkyl, aryl, alkaryl, or aralkyl group containing 1-10 carbons, e.g., methyl, ethyl, propyl, cyclohexyl, phenyl, tolyl, benzyl, etc. Particularly preferred halonaphthalenes are 6-alkoxy-5-bromo-1-cyanonaphthalenes, 6-alkoxy-5-iodo-1-cyanonaphthalenes, 6-alkoxy-5-bromo-1-naphthoates, and 6-alkoxy-5-iodo-1-naphthoates, especially those compounds wherein the alkoxy groups are methoxy.

The halonaphthoates are known compounds. The halocyanonaphthalenes are compounds that can be prepared by cyanating the appropriately substituted tetralone, e.g., 6-methoxytetralone, to form the appropriately substituted 1-cyano-3,4-dihydronaphthalene, e.g., 6-methoxy-1-cyano-3,4-dihydronaphthalene, aromatizing the product in any suitable manner, and brominating or iodinating the resultant substituted 1-cyanonaphthalene by known techniques.

The amount of potassium trifluoroacetate reacted with the aromatic halide is not critical and may be a considerable excess, such as the amounts of sodium trifluoroacetate that have been employed in the past. However, since such large amounts of potassium trifluoroacetate are not required, the amount used is generally in the range of about 1-3 equivalents, most commonly about 1.5-2 equivalents.

Dipolar aprotic solvents that may be utilized include, e.g., N-methylpyrrolidone, N,N-dimethylformamide, N,N-dimethylacetamide, hexamethylphosphoric triamide, dimethylsulfoxide, etc. The particular solvent employed does not appear to be critical except in the sense that it should have an appropriate boiling point for use at the reaction temperatures to be utilized, but the preferred solvents are N,N-dimethylformamide and N,N-dimethylacetamide. The solvent is used in solvent amounts, e.g., an amount such as to provide an organic solids concentration of up to about 15%.

The cuprous iodide may be employed in any suitable amount, generally an amount in the range of about 0.5–5 equivalents.

The reaction is conducted by combining the ingredients in any convenient order and heating them at a suitable temperature, conveniently reflux temperature, to accomplish the desired trifluoromethylation. Anhydrous conditions are preferably employed, and the temperature is generally in the range of about 130°–160° C., preferably about 140°–155° C.

After completion of the reaction, the product may be recovered by conventional techniques and/or subjected to further reactions to form derivatives. For example, products obtained by trifluoromethylating the preferred halocyanonaphthalenes and halonaphthoates can be subjected to reactions such as those taught by Sestanj et al. in U.S. Pat. No. 4,439,617. Thus, e.g., (1) a (trifluoromethyl)cyanonaphthalene or trifluoromethylnaphthoate prepared by the trifluoromethylation reaction may be hydrolyzed to the corresponding acid in the presence of a base such as sodium or potassium hydroxide, (2) the acid can be halogenated, e.g., by reaction with thionyl chloride, to form the corresponding acid halide, (2) the acid halide may be reacted with a saturated hydrocarbyl ester of an acid corresponding to the formula ZNHCH$_2$COOH (e.g., methyl, ethyl, propyl, cyclohexyl, phenyl, tolyl, or benzyl sarcosinate, the corresponding esters of aminoacetic acids having other N-substituents containing 1-6 carbons, such as N-ethyl, N-propyl, etc.) to form an amide corresponding to the formula:

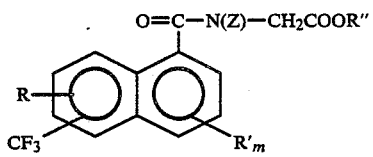

and (3) the amide may be thiated, e.g., with phosphorus pentasulfide or the like, and the product saponified and hydrolyzed to form a thioamide corresponding to the formula:

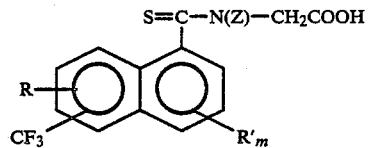

The invention is advantageous in that it permits trifluoromethylaromatic compounds to be prepared in high yields from the corresponding aromatic bromides or iodides at a faster rate and with the use of less reagent than is required when sodium trifluoroacetate is employed. Also, the reaction is more selective than the sodium trifluoroacetate reaction, so the product is less contaminated with by-product. Additionally, the potassium trifluoroacetate reactions can be accomplished with higher concentrations of solids than are operable when sodium trifluoroacetate is used, and the reactor productivity can thus be increased considerably.

The following examples are given to illustrate the invention and are not intended as a limitation thereof.

COMPARATIVE EXAMPLE A

A mixture of one molar proportion of 6-methoxy-5-iodo-1-cyanonaphthalene (6-MICN), 2.3 molar proportions of sodium trifluoroacetate, and 1.9 molar proportions of CuI was stirred into molar proportions of toluene, after which about 82 molar proportions of the toluene were stripped at 111° C. Then 83 molar proportions of dry N,N-dimethylacetamide (DMAC) were added, and the mixture was heated while distilling over the remainder of the toluene until the temperature reached 152° C. Heating was stopped, another 0.7 molar proportion of sodium trifluoroacetate was added, and the reaction mixture was heated back up to 152° C. and stirred for 80 minutes at 152°–155° C. to give a total reaction time of four hours. After cooling and workup, GC analysis showed the reaction mixture to contain 97.25 area % of the desired 6-methoxy-5-trifluoromethyl-1-cyanonaphthalene (6-MTCN).

COMPARATIVE EXAMPLE B

Comparative Example A was essentially repeated except that the 6-MICN was replaced with 6-methoxy-5-bromo-1-cyanonaphthalene (6-MBCN) and the total reaction time was 6 hours. GC analysis of the final reaction mixture showed 93.45 area % of 6-MTCN.

COMPARATIVE EXAMPLE C

Using the same general procedure as in Comparative Example A, one molar proportion of methyl 6-methoxy-5-bromo-1-naphthoate (MMBN) was reacted with 1.7 molar proportions of sodium trifluoroacetate in the presence of 2 molar proportions of CuI and molar proportions of N,N-dimethylformamide (DMF), with an additional 0.95 molar proportion of sodium trifluoroacetate being added during the course of the reaction. The total reaction time was 5 hours. After workup, the desired methyl 6-methoxy-5-trifluoromethyl-1-naphthoate (MMTN) was isolated in a 76% yield.

COMPARATIVE EXAMPLE D

A mixture of one molar proportion of 4-bromodiphenyl ether, 1.99 molar proportions of CuI, and 1.7 molar proportions of sodium trifluoroacetate was stirred into 14 molar proportions of toluene, after which part of the toluene was stripped, 46 molar proportions of DMF were added, and the reaction mixture was heated up to 149° C. for three hours. Heating was stopped, another molar proportion of sodium trifluoroacetate was added, and the mixture was heated up to 149° C. for two hours. GC analysis of the product showed 47.5 area % of the desired 4-trifluoromethyldiphenyl ether, 26.5 area % of perfluoroalkyl homologs, and 22.8 area % of unreacted 4-bromodiphenyl ether.

EXAMPLE I

A mixture of one molar proportion of 6-MICN, 1.9 molar proportions of CuI, and 1.7 molar proportions of potassium trifluoroacetate was stirred into 10 molar proportions of toluene after which part of the toluene was stripped, 40 molar proportions of DMF were added, and toluene and DMF were stripped until the temperature reached 149° C. The temperature was maintained at 149°-150° C. for two hours, after which GC analysis showed that all of the 6-MICN had been converted and more than 98% had been converted to 6-MTCN.

EXAMPLE II

A mixture of one molar proportion of 6-MBCN, 2 molar proportions of CuI, and 1.7 molar proportions of potassium trifluoroacetate was stirred into 15 molar proportions of toluene, after which part of the toluene was stripped and 66 molar proportions of DMF were added. The reaction mixture was heated at 140°-150° C. for about 3.5 hours, cooled, worked up, and subjected to GC analysis. The analysis showed substantially 100% conversion to 6-MTCN and a trace formation of by-product.

EXAMPLE III

Example II was essentially repeated except that the solids concentration was doubled. Similar results were observed.

EXAMPLE IV

Example II was essentially repeated except that the amount of potassium trifluoroacetate used was 1.5 molar proportions, and 53 molar proportions of DMF were substituted for the DMAC. The GC analysis showed 99.77 area % of 6-MTCN.

EXAMPLE V

Comparative Example C was essentially repeated except that the initial sodium trifluoroacetate was replaced with 1.75 molar proportions of potassium trifluoroacetate, no additional trifluoroacetate was added during the course of the reaction, and the reaction time was only 3.5 hours. GC analysis showed a conversion of 99.8%, and the isolated yield of product was 86%.

EXAMPLE VI

Comparative Example D was essentially repeated except that the initial sodium trifluoroacetate was replaced with 2.69 proportions of potassium trifluoroacetate, no additional trifluoroacetate was added during the course of the reaction, and the reaction time was 3.5 hours. GC analysis of the product showed 67 area % of the desired 4-trifluoromethyldiphenyl ether, 16.6 area % of perfluoroalkyl homologs, and 16.2 area % of unreacted 4-bromodiphenyl ether.

It is obvious that many variations may be made in the products and processes set forth above without departing from the spirit and scope of this invention.

What is claimed is:

1. In a process for preparing a trifluoromethylaromatic compound by reacting an aromatic bromide or iodide with a trifluoroacetate in the presence of cuprous iodide and a dipolar aprotic solvent, the improvement which comprises employing potassium trifluoroacetate as the trifluoroacetate.

2. The process of claim 1 wherein the aromatic halide is a bromide.

3. The process of claim 1 wherein the aromatic halide is an iodide.

4. The process of claim 1 wherein the aromatic halide is a halonaphthalene corresponding to the formula:

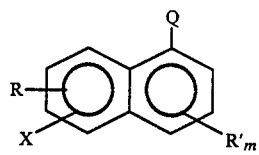

wherein R and R' are independently selected from chloro, fluoro, nitro, hydroxy, and alkyl and alkoxy substituents containing 1-6 carbons; Q is —CN or —COOR"; R" is saturated hydrocarbyl; X is bromo or iodo; and m is 0 or 1.

5. The process of claim 4 wherein the aromatic halide is a 6-alkoxy-5-bromo-1-cyanonaphthalene.

6. The process of claim 4 wherein the aromatic halide is a 6-alkoxy-5-iodo-1-cyanonaphthalene.

7. The process of claim 4 wherein the aromatic halide is a 6-alkoxy-5-bromo-1-naphthoate.

8. The process of claim 4 wherein the aromatic halide is a 6-alkoxy-5-iodo-1-naphthoate.

9. The process of claim 1 wherein the reaction is conducted at about 130°-160° C.

10. The process of claim 9 wherein the reaction is conducted at about 140°-155° C.

11. The process of claim 1 wherein the aromatic halide is reacted with about 1-3 equivalents of potassium trifluoroacetate.

12. The process of claim 1 wherein the solvent is N,N-dimethylformamide.

13. The process of claim 1 wherein the solvent is N,N-dimethylacetamide.

14. A process which comprises reacting a halonaphthalene corresponding to the formula:

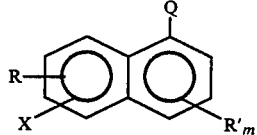

wherein R and R' are independently selected from chloro, fluoro, nitro, hydroxy, and alkyl and alkoxy substituents containing 1-6 carbons; Q is —CN or —COOR"; R" is saturated hydrocarbyl; X is bromo or iodo; and m is 0 or 1, with about 1-3 equivalents of potassium trifluoroacetate in the presence of a dipolar aprotic solvent and about 0.5-5 equivalents of cuprous iodide at about 140°-155° C. so as to form a trifluoromethylaromatic compound.

15. The process of claim 14 wherein the solvent is N,N-dimethylformamide.

16. The process of claim 14 wherein the solvent is N,N-dimethylacetamide.

17. The process of claim 14 wherein the halonaphthalene is a 6-alkoxy-5-bromo-1-cyanonaphthalene.

18. The process of claim 14 wherein the halonaphthalene is a 6-alkoxy-5-iodo-1-cyanonaphthalene.

19. The process of claim 14 wherein the halonaphthalene is a 6-alkoxy-5-bromo-1-naphthoate.

20. The process of claim 14 wherein the halonaphthalene is a 6-alkoxy-5-iodo-1-naphthoate.

* * * * *

UNITED STATES PATENT AND TRADEMARK OFFICE
CERTIFICATE OF CORRECTION

PATENT NO. : 4,808,748
DATED : February 28, 1989
INVENTOR(S) : Ronny W. Lin et al It is certified that error appears in the above-identified patent and that said Letters Patent is hereby corrected as shown below:

Column 4, line 10, reads "into molar proportions" and should read -- into 146 molar proportions --.

Column 4, line 38, reads "and molar" and should read -- and 46 molar --.

Signed and Sealed this

Twenty-second Day of August, 1989

Attest:

DONALD J. QUIGG

Attesting Officer

Commissioner of Patents and Trademarks